(12) United States Patent
Seto et al.

(10) Patent No.: US 6,335,979 B1
(45) Date of Patent: Jan. 1, 2002

(54) MEDICAL IMAGING APPARATUS

(75) Inventors: Hiromitsu Seto; Tomoyasu Komori, both of Otawara (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/199,491

(22) Filed: Nov. 25, 1998

(30) Foreign Application Priority Data

Nov. 28, 1997 (JP) .............................. 9-329215

(51) Int. Cl.⁷ .................................. G06K 9/00
(52) U.S. Cl. ........................ 382/128; 128/781
(58) Field of Search ............. 128/781; 378/91; 382/226, 128, 129, 130; 395/127

(56) References Cited

U.S. PATENT DOCUMENTS

| | | | | |
|---|---|---|---|---|
| 5,018,178 A | * | 5/1991 | Katsumata | 378/91 |
| 5,099,859 A | * | 3/1992 | Bell | 128/781 |
| 5,231,651 A | | 7/1993 | Ozaki et al. | |
| 5,661,820 A | * | 8/1997 | Legelmeyer | 382/226 |
| 5,706,416 A | * | 1/1998 | Mann et al. | 395/127 |

FOREIGN PATENT DOCUMENTS

JP 5-68680 3/1993

* cited by examiner

Primary Examiner—Joseph Mancuso
Assistant Examiner—Abolfazl Tabatabai
(74) Attorney, Agent, or Firm—Oblon, Spivak, McClelland, Maier & Neustadt, P.C.

(57) ABSTRACT

A list of a plurality of reference images is displayed. Parameters pertaining to signal acquisition, image generation, and image display are related to each of these reference images. When the operator selects one desired reference image from the list, a signal is acquired and an image is generated and displayed in accordance with the parameters related to the selected reference image. The only operation which the operator must perform is to select a reference image visually close to a desired medical image. The apparatus automatically sets detailed signal acquisition parameters, image generation parameters, and image display parameters which the operator need not know.

15 Claims, 4 Drawing Sheets

MEDICAL IMAGING APPARATUS

BACKGROUND OF THE INVENTION

1. Field of the Invention

The present invention relates to a medical imaging apparatus such as an X-ray computer tomography apparatus (X-ray CT), magnetic resonance diagnostic apparatus, nuclear medicine diagnostic apparatus, or ultrasonic diagnostic apparatus.

2. Discussion of the Background

Imaging an object with a medical imaging apparatus requires preparations. In these preparations, the operator sets signal acquisition conditions including a few tens of parameters. The number of these parameters is steadily increasing with the recent increasing number of functions.

The signal acquisition conditions (scan conditions) of an X-ray CT include parameters such as a scan type (single slice scan/helical scan (volume scan)), slice thickness, slice interval, volume size, gantry tilt angle, tube voltage, tube current, imaging region size, and scan speed.

It is very inefficient and unrealistic to manually set each of several or several tens of parameters as described above each time imaging is performed. For this reason, a preset function is used. This preset function stores signal acquisition parameter sets recommended by the manufacturer and signal acquisition parameter sets used in the past and immediately reproduces any of these parameter sets in response to button operation. That is, a signal is acquired in accordance with the signal acquisition parameter set selected by the operator.

The problem with this preset function is that the number of these preset buttons cannot be simply increased. The principal reason is that although the number of preset buttons can be easily increased to, e.g., 100, this makes the correspondence between these preset buttons and signal acquisition conditions very difficult to understand. As a consequence, the convenience of this function lowers.

Additionally, the number of functions of image generation and image display is increasing with the resent increase in number of signal acquiring functions. This enormously increases the number of image generation parameters and image display parameters which the operator must, or can, designate.

Accordingly, the present situation is that the setting of image generation parameters and image display parameters requires a long time and this cancels out the ease with which signal acquisition parameters are set by the preset function. That is, to reduce the time which the operator takes to make preparations, it is necessary to reduce not only the time to set signal acquisition parameters but also the time to set image generation parameters and image display parameters.

Unfortunately, it is impossible to prepare preset buttons not only for an enormous number of signal acquisition parameters but also for image generation parameters and image display parameters. This is so because no operator can understand the correspondence between these preset buttons and registered parameter sets pertaining to signal acquisition, image generation, and image display.

SUMMARY OF THE INVENTION

It is an object of the present invention to provide a medical imaging apparatus such as an X-ray computer tomography apparatus (X-ray CT), magnetic resonance diagnostic apparatus, nuclear medicine diagnostic apparatus, or ultrasonic diagnostic apparatus, by which the operator can easily set, in a readily understandable way, a huge number of parameters necessary for processes from signal acquisition to image generation and image display.

The present invention achieves the following effects. First, a list of a plurality of reference images is displayed. Parameters pertaining to signal acquisition, image generation, and image display are related to each of these reference images. When the operator selects one desired reference image from the list, a signal is acquired and an image is generated and displayed in accordance with parameters related to the selected reference image. The only operation which the operator must perform is to select a reference image visually close to a desired medical image. The apparatus automatically sets detailed signal acquisition parameters, image generation parameters, and image display parameters which the operator need not know.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
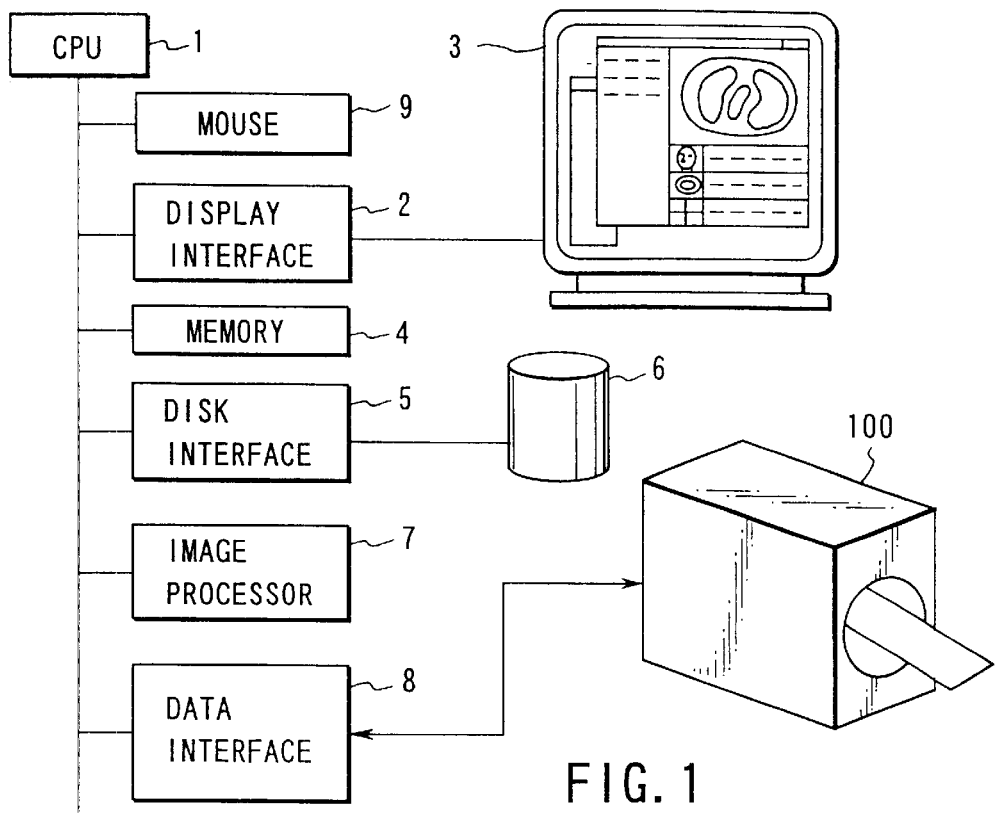
FIG. 1 is a block diagram showing the arrangement of a medical imaging apparatus according to an embodiment of the present invention.

Referring now to the drawings, wherein like reference numerals designate identical or corresponding parts throughout the several views, and more particularly to FIG. 1 thereof, there is illustrated an exemplary block diagram showing the hardware configuration of a medical imaging apparatus according to an embodiment of the present invention.

As shown in FIG. 1, the medical imaging apparatus of this embodiment includes a central processing unit (CPU) 1, a display interface 2, a display 3, a memory 4, a disk interface 5, a disk unit 6, an image processor 7, a data interface 8, a mouse 9, and a data acquisition unit 100.

If the present invention is considered as a parameter setting support system for a medical imaging apparatus, this parameter setting support system includes the central processing unit (CPU) 1, the display interface 2, the display 3, the memory 4, the disk interface 5, the disk unit 6, the image processor 7, and the data interface 8, except for the data acquisition unit 100. In this embodiment, however, the present invention will be described as a medical imaging apparatus.

This medical imaging apparatus is one of an X-ray computer tomography apparatus (X-ray CT), magnetic resonance diagnostic apparatus (MRI), nuclear medicine diagnostic apparatus (gamma camera), or ultrasonic diagnostic apparatus. Any of these medical imaging apparatuses basically has a function (signal acquiring function) of acquiring a signal as an original of an image from an object, a function (image generating function) of generating a medical image from the acquired signal, and a function (image display function) of displaying the generated medical image by, e.g., zooming and/or coloring the image.

For the sake of simplicity of explanation, assume that this medical imaging apparatus is an X-ray computer tomography apparatus. On this assumption, the data acquisition unit 100 is a scanner including an X-ray tube, X-ray detector, rotating mechanism, DAS (data acquisition system), and the like.

When this scanner 100 acquires projection data of an object by scanning, this projection data is supplied to the image processor 7 via the data interface 8. The image processor 7 reconstructs tomographic image data. In addition to this tomographic image data reconstructing function, the image processor 7 has a function of constructing, e.g., three-dimensional image data and maximum value projection (MIP) image data, and a function of generating reference image data (to be described later) from, e.g., the tomographic image data or three-dimensional image data. The tomographic image data obtained by the image processor 7 is supplied to and stored in the disk unit 6 via the disk interface 5.

Also, as will be described later, the reference image data generated by the image processor 7 is related to a plurality of signal processing, image generation, and image display parameter data and to title data, and supplied to and stored in the disk unit 6 via the disk interface 5.

When the operator makes preparations, the reference image data and title data stored in the disk unit 6 are read out from the disk unit 6 and displayed in the form of a list on the display 3 via the display interface 2. The apparatus has the mouse 9 or an equivalent pointing device to allow the operator to selectively designate a desired one of the reference images on the list. The CPU 1 loads from the disk interface 8 signal acquisition parameters, image generation parameters, and image display parameters related to the reference image designated by using the mouse 9. The CPU 1 sets the signal acquisition conditions of the scanner 100, the image generation conditions of the image processor 7, and the image display conditions of the display interface 2 in accordance with the loaded signal processing parameters, image generation parameters, and image display parameters, respectively.

As described previously, a plurality of parameters relate to the projection data acquisition by the scanner 100. Analogously, a plurality of parameters relate to each of an image generation process of generating a tomographic image from an acquired signal and an image display process of displaying a reconstructed tomographic image. Examples of the signal acquisition parameters are a portion to be imaged (e.g., a whole body, head, chest, lung, or lower limb), scan type (single slice scan/multi-slice scan/helical scan (volume scan)), slice thickness, slice interval, volume size, gantry tilt angle, tube voltage, tube current, imaging region size, scan speeds (rotating speeds of an X-ray tube and detector), and bed moving amount which is the moving amount of a bed which moves while the X-ray tube rotates once. Examples of the image generation parameters are a reconstruction method (two-dimensional/three-dimensional), reconstruction region size, reconstruction matrix size, and threshold value for extracting a portion of interest. Examples of the image display parameters are a window level, window width, display magnification, and multi-planar (sagittal/coronal/oblique).

To accomplish the whole inspection sequence from signal acquisition to final image display through image generation, it is necessary to set the signal acquisition parameters, image generation parameters, and image display parameters described above. Note that these signal acquisition parameters, image generation parameters, and image display parameters will be generally called a plan. That is, if these signal acquisition parameters, image generation parameters, and image display parameters are previously registered as a plan, the whole inspection sequence can be readily executed only by selecting the plan.

In this embodiment, a plurality of plans are registered in the disk unit 6. The operator selectively designates a desired one of these registered plans by using the mouse 9 and thereby can immediately set not only signal acquisition parameters but also image generation parameters and image display parameters which cannot be immediately set in conventional systems.

Additionally, to selectively designate a desired plan, the operator must understand the relationship between each plan, i.e., parameters contained in the plan, and a finally obtained medical image. Since each plan contains a few tens of parameters to, in some instances, a few hundred parameters pertaining to signal acquisition, image generation, and image display, it is ineffective to present full text of these parameters to the operator.

Figure 2:
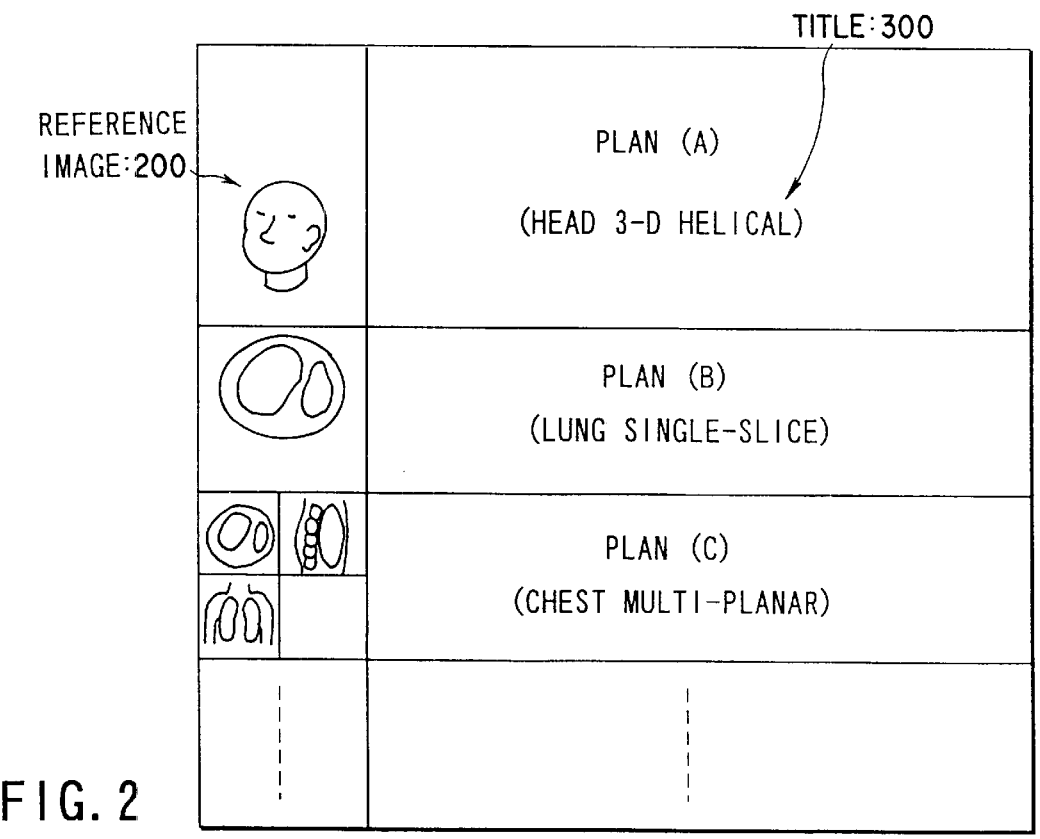
FIG. 2 is a view showing a plan list displayed on a display shown in FIG. 1.

In this embodiment, therefore, as shown in FIG. 2, the relationship between each plan and a finally obtained medical image is provided by a reference image 200 and a title 300.

The reference image 200 is a reduced or diagramatic medical image in common with all or some of signal acquisition parameters, image generation parameters, and image display parameters forming a plan corresponding to the reference image. That is, each reference image is provided as information suggesting a medical image in common with all or some of signal acquisition parameters, image generation parameters, and image display parameters related to the reference image. Accordingly, the operator can assess from a reference image a medical image that is going to be finally obtained by signal acquisition parameters, image generation parameters, and image display parameters related to the reference image.

The title 300 represents at least some characteristic parameters, e.g., a portion, scan type, and reconstruction method, which may be useful to select a plan corresponding to the title 300, among other signal acquisition parameters, image generation parameters, and image display parameters forming the plan.

Figure 3:
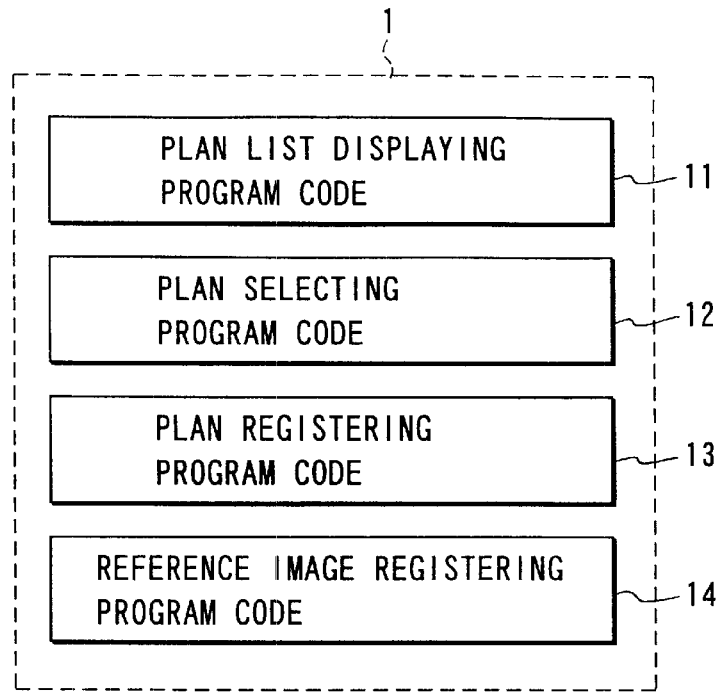
FIG. 3 is a view showing the types of program codes executed by a CPU shown in FIG. 1.

As shown in FIG. 3, program codes 11, 12, 13, and 14 executable by the CPU 1 implement or support functions of displaying a plan list, selecting and registering plans, and registering reference images. However, these functions can also be implemented by hardware.

Figure 4:
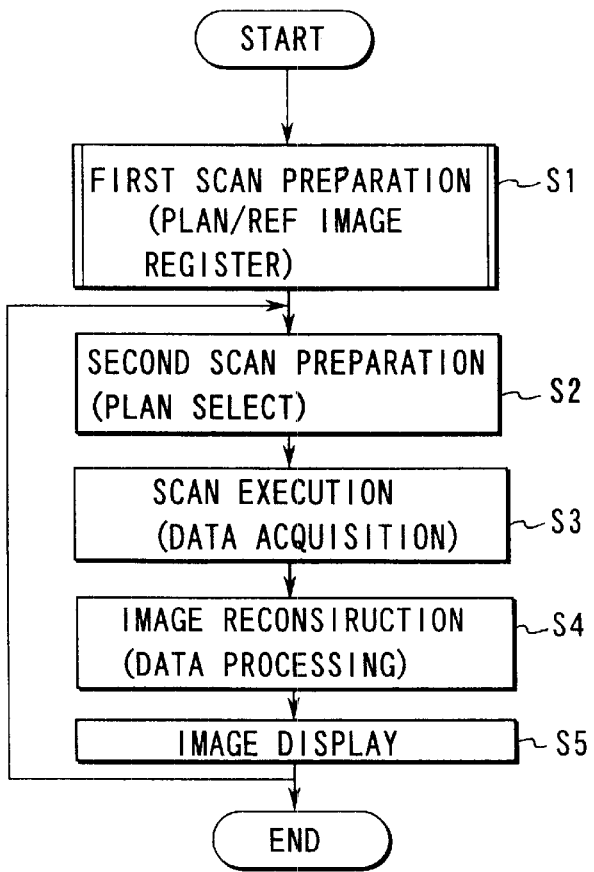
FIG. 4 is a flow chart showing the procedure from preparations to image display in this embodiment.
Figure 5:
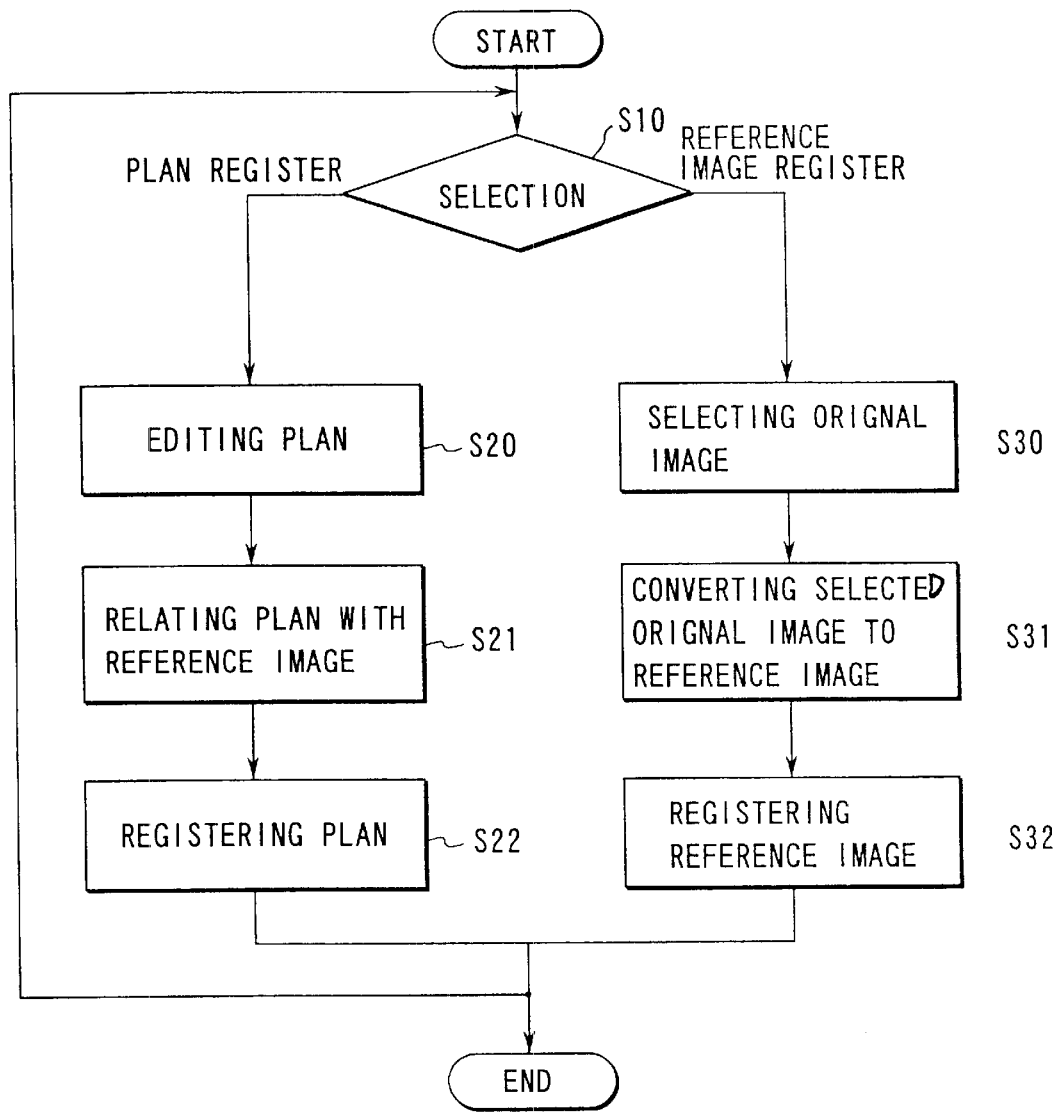
FIG. 5 is a flow chart showing the process flow of a first preparation shown in FIG. 4.

FIG. 4 is a flow chart showing the basic operation of the medical imaging apparatus with the above arrangement. First, a first preparation is performed (step S1). This first preparation relates to register of plans and reference images. FIG. 5 is a flow chart of this first preparation. In step S10, a user selects one of plan register and reference image register.
(Reference image register)

Figure 6:
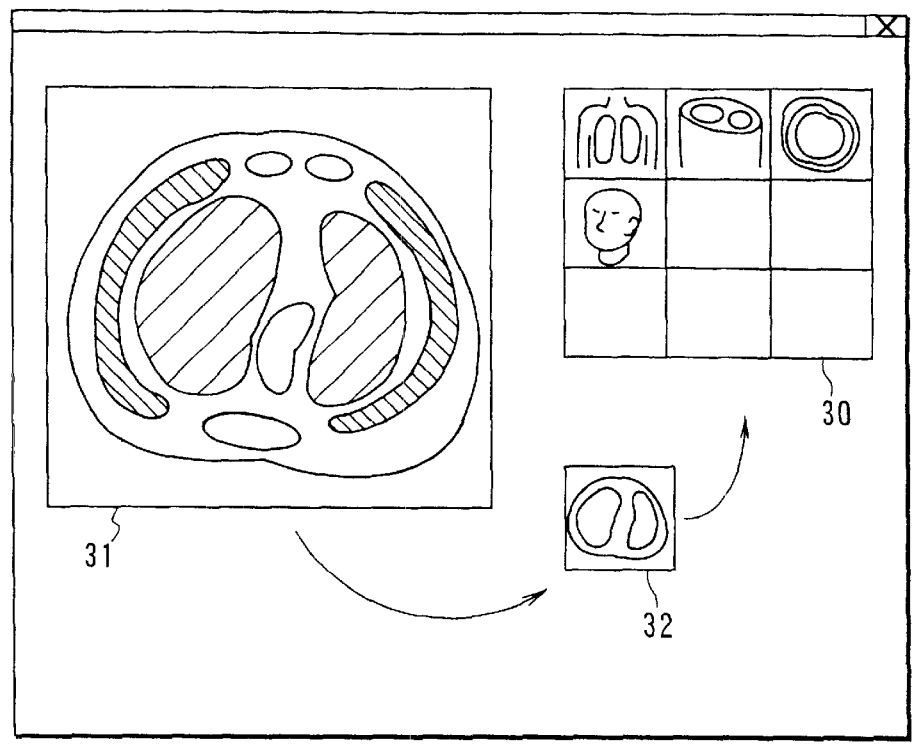
FIG. 6 is a view showing a reference image register screen shown in FIG. 5.

FIG. 6 is a view showing a reference image register screen. This reference image register is executed by the reference image registering program code 14 of the CPU 1. First, in step S30, an original image 31 for forming a reference image is selected from preinstalled medical images and medical images actually sensed in the past. In step S31, the image processor 7 converts the selected original image 31 into a reference image 32. For example, this reference image 31 is a reduced image of the original image 31 or a diagramatic image obtained by graphically processing the original image 31. In step S32, the reference image 32 is registered in a reference image candidate list 30 and stored in the disk unit 6. Note that this reference image can be either a still image or motion image.
(Plan Register)

When plan register is chosen in step S10 of FIG. 5, plan edit is executed (step S20). In this plan edit, the operator designates each of a plurality of parameters concerning signal acquisition, image generation, and image display. Alternatively, signal acquisition parameters, image generation parameters, and image display parameters used in the past are used directly or after being slightly modified.

Figure 7:
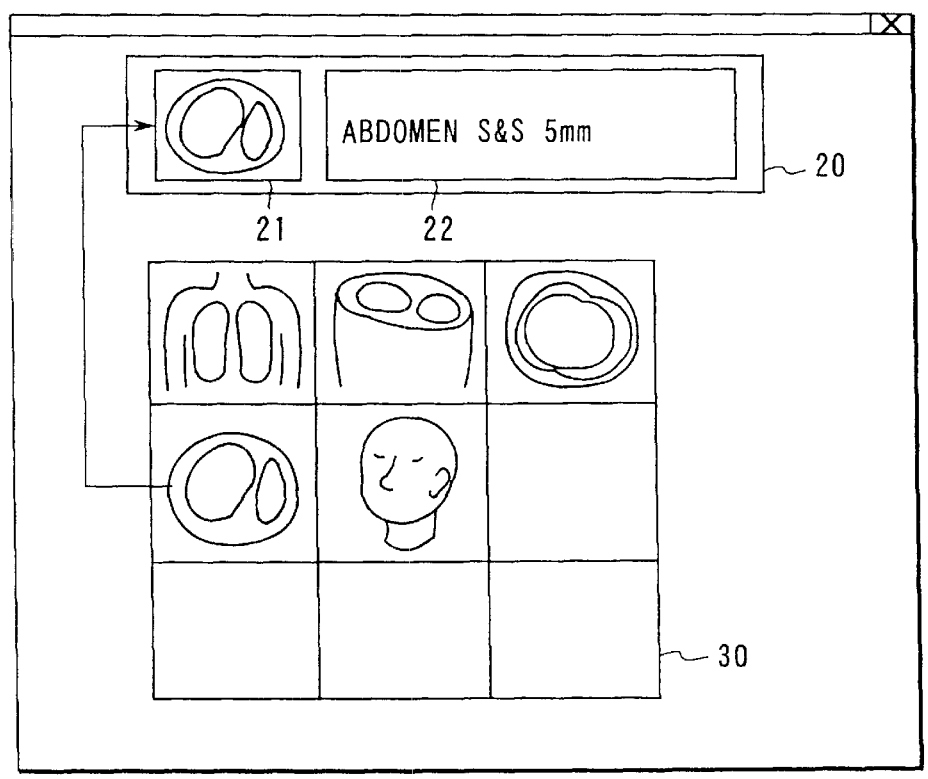
FIG. 7 is a view showing a plan register screen shown in FIG. 5.

In step S21, a reference image is related to the edited plan. In this process, the operator selects an arbitrary reference image 21 from the reference image candidate list 30 as shown in FIG. 7. A title 20 is also automatically or manually input.

In step S22, the edited plan is stored in the disk unit 6. In this step, the selected reference image 21 and the input title 20 are related to the plan.

After this first preparation S1, a second preparation S2 is started. This second preparation S2 is performed immediately before imaging is started. In the second preparation S2, the operator selectively designates a desired plan from the plans registered in the first preparation SI.

In this second preparation, as shown in FIG. 2, the plan list is displayed together with the reference images 200 and the titles 300 on the display 3. The operator checks these reference images 200 and titles 300 and selectively designates a desired plan from this plan list by double-clicking the display area of a corresponding reference image 200 or title 300 by using a mouse button.

When a plan is selected, the CPU 1 loads from the disk unit 6 signal acquisition parameters, image generation parameters, and image display parameters related to the reference image 200 of the plan.

In accordance with the loaded signal processing parameters, image generation parameters, and image display parameters, the scanner 100 executes signal acquisition (step S3), the image processor 7 generates (reconstructs) a medical image (tomographic image) (step S4), and the display 3 displays this medical image, respectively.

In this embodiment as described above, a plurality of reference images are first displayed in the form of a list. Parameters pertaining to signal acquisition, image generation, and image display are related to each of these reference images. When the operator selects one desired reference image from the list, a signal is acquired and an image is generated and displayed in accordance with parameters related to the selected reference image.

Each reference image suggests medical images sharing all or some of a plurality of parameters. From such reference images, therefore, the operator can assess medical images that are going to be finally obtained in accordance with parameters related to these reference images and selectively designate a desired plan.

Accordingly, the only operation which the operator must perform is to select a reference image visually close to a desired medical image. The apparatus automatically sets detailed signal acquisition parameters, image generation parameters, and image display parameters which the operator need not know.

The present invention is not limited to the above embodiment, so various modifications of the invention are possible. For example, in the above embodiment, pairs of reference images and titles are displayed. However, only a reference image list can be displayed without displaying any title list, or only a title list can be displayed without displaying any reference image list.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. A medical imaging apparatus comprising:
   means for storing a plurality of generic reference images, a plurality of parameters pertaining to signal acquisition, image generation, and image display being related to each of the generic reference images;
   means for displaying a list of the stored reference images;
   means for allowing the operator to selectively designate an arbitrary one of the displayed generic reference images; and
   means for acquiring a signal from an object, generating a medical image from the acquired signal, and displaying the generated image in accordance with parameters related to the designated generic reference image.

2. An apparatus according to claim 1, wherein each generic reference image is a reduced image suggesting a medical image in common with all parameters related to the generic reference image.

3. An apparatus according to claim 1, wherein each generic reference image is a reduced image suggesting a medical image in common with some of a plurality of parameters related to the medical image.

4. An apparatus acing to claim 1, wherein each reference image is a diagramatic image suggesting a medical image in common with all parameters related to the generic reference image.

5. An apparatus according to claim 1, wherein each generic reference image is a diagramatic image suggesting a medical image in common with some of a plurality of parameters related to the medical image.

6. An apparatus according to claim 1, wherein each generic reference image has a smaller data amount than a data amount of a medical image.

7. An apparatus according to claim 1, wherein each generic reference image is displayed together with a tide containing some of a plurality of parameters related to the generic reference image.

8. An apparatus according to claim 1, further comprising: means for processing an actually imaged medical image into a generic reference image; and means for storing the processed generic reference image by relating thereto signal acquisition parameters, image generation parameters, and image display parameters used to obtain the actually imaged medical image.

9. A medical imaging apparatus comprising: means for storing a plurality of generic reference images, a plan containing a plurality of parameters pertaining to signal acquisition, image generation, and image display be related to each of the generic reference images, and each generic reference image representing a plan related to the generic reference image;

means for displaying a list of the stored generic reference images;

means for allowing an operator to selectively designate an arbitrary one of the displayed generic reference images; and means for acquiring a signal, generating a medical image from the acquired signal, and displaying the generated medical image in accordance with parameters contained in a plan related to the designated generic reference image.

10. A parameter setting support system for a medical imaging apparatus, comprising: means for storing a plurality of generic reference images, a plurality of parameters pertaining to signal acquisition, image generation, and image display being related to each of the generic reference images, and each generic reference image representing a medical image in common with at least some of the parameters; means for displaying a list of the stored generic reference images; means for allowing an operator to selectively designate an arbitrary one of the displayed generic reference images; and means for outputting parameters related to the designated generic reference image to a medical imaging apparatus.

11. A parameter setting support system for a medical imaging apparatus comprising:

means for storing a plurality of generic reference images, a plan containing a plurality of parameters pertaining to signal acquisition, image generation, and image display being related to each of the generic reference images, and each generic reference image representing a plan related to the generic reference image;

means for displaying a list of the stored generic reference images;

means for allowing an operator to selectively designate an arbitrary one of the displayed generic reference images; and means for outputting parameters of a plan related to the designated generic reference image to a medical imaging apparatus.

12. An apparatus according to claim 1, wherein said plurality of generic reference images correspond to one of a generic image of a whole body, a generic image of a head, a generic image of a chest, a generic image of a lung, a generic image of a limb.

13. A medical imaging apparatus according to claim 9, wherein said plurality of generic reference images correspond to one of a generic image of a whole body, a generic image of a head, a generic image of a chest, a generic image of a lung, a generic image of a limb.

14. A parameter setting support system for a medical imaging apparatus according to claim 10, wherein said plurality of generic reference images correspond to one of a generic image of a whole body, a generic image of a head, a generic image of a chest, a generic image of a lung, a generic image of a limb.

15. A parameter setting support system for a medical imaging apparatus according to claim 11, wherein said plurality of generic reference images correspond to one of a generic image of a whole body, a generic image of a head, a generic image of a chest, a generic image of a lung, a generic image of a limb.

* * * * *